US010408773B2

(12) United States Patent
Chen et al.

(10) Patent No.: US 10,408,773 B2
(45) Date of Patent: Sep. 10, 2019

(54) PREDICTING TOTAL ORGANIC CARBON (TOC) USING A RADIAL BASIS FUNCTION (RBF) MODEL AND NUCLEAR MAGNETIC RESONANCE (NMR) DATA

(71) Applicant: HALLIBURTON ENERGY SERVICES, INC., Houston, TX (US)

(72) Inventors: Songhua Chen, Katy, TX (US); Wei Shao, Conroe, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 21 days.

(21) Appl. No.: 15/521,859

(22) PCT Filed: Nov. 25, 2014

(86) PCT No.: PCT/US2014/067296
§ 371 (c)(1),
(2) Date: Apr. 25, 2017

(87) PCT Pub. No.: WO2016/085466
PCT Pub. Date: Jun. 2, 2016

(65) Prior Publication Data
US 2017/0241921 A1    Aug. 24, 2017

(51) Int. Cl.
*G01V 3/00* (2006.01)
*G01N 24/08* (2006.01)
(Continued)

(52) U.S. Cl.
CPC ........... *G01N 24/081* (2013.01); *E21B 49/00* (2013.01); *E21B 49/02* (2013.01); *G01N 15/088* (2013.01);
(Continued)

(58) Field of Classification Search
CPC .... G01R 33/448; G01R 33/50; G01V 99/005; G01V 3/32; G01V 1/00; G01V 11/002;
(Continued)

(56) References Cited

U.S. PATENT DOCUMENTS 7,091,719 B2    8/2006  Freedman
2005/0242807 A1* 11/2005 Freedman .............. G01V 11/00
                                                      324/303
(Continued)

FOREIGN PATENT DOCUMENTS

WO    2015/088542    6/2015
WO    2015/088543    6/2015

OTHER PUBLICATIONS

PCT International Search Report and Written Opinion, dated Aug. 20, 2015, Appl No. PCT/US2014/067296, "Predicting Total Organic Carbon (TOC) Using a Radial Basis Function (RBF) Model and Nuclear Magnetic Resonance (NMR) Data," Filed Nov. 25, 2014, 15 pgs.

*Primary Examiner* — Rodney E Fuller
(74) *Attorney, Agent, or Firm* — Gilliam IP PLLC

(57) ABSTRACT

Systems, methods, and software for predicting total organic carbon (TOC) values are described. A representative method includes obtaining nuclear magnetic resonance (NMR) data and training a radial basis function (RBF) model based on the NMR data and measured total organic carbon (TOC) values. The method also includes obtaining subsequent NMR data and employing the trained RBF model to predict TOC values based at least in part on the subsequent NMR data. The method also includes storing or displaying the predicted TOC values.

20 Claims, 8 Drawing Sheets

(51) Int. Cl.
  *E21B 49/00* (2006.01)
  *G01R 33/44* (2006.01)
  *E21B 49/02* (2006.01)
  *G01N 15/08* (2006.01)
  *G01N 23/223* (2006.01)
  *E21B 47/12* (2012.01)

(52) U.S. Cl.
  CPC ......... *G01N 23/223* (2013.01); *G01R 33/448* (2013.01); *E21B 47/12* (2013.01)

(58) Field of Classification Search
  CPC .. G01V 1/40; G01V 1/50; E21B 49/00; E21B 49/02; E21B 49/12; E21B 49/005; E21B 49/006; G01N 33/24
  USPC ....................................................... 324/303
  See application file for complete search history.

(56) References Cited

U.S. PATENT DOCUMENTS

| | | |
|---|---|---|
| 2005/0270023 A1 | 12/2005 | Freedman |
| 2006/0290350 A1 | 12/2006 | Hursan et al. |
| 2011/0144913 A1* | 6/2011 | Klein ................ G01V 3/20 702/13 |
| 2012/0065888 A1 | 3/2012 | Wu et al. |
| 2014/0214324 A1 | 7/2014 | Freedman et al. |
| 2014/0253116 A1 | 9/2014 | Freedman et al. |
| 2015/0081265 A1* | 3/2015 | Kauerauf ........... G06F 17/5009 703/10 |
| 2016/0003037 A1* | 1/2016 | Khalid ................ E21B 49/00 73/152.05 |
| 2017/0235016 A1* | 8/2017 | Prioul ................ E21B 49/005 73/152.01 |
| 2017/0322337 A1* | 11/2017 | Prasad ................ G01V 3/32 |
| 2018/0031732 A1* | 2/2018 | Mosse ................ G01V 1/50 |

* cited by examiner

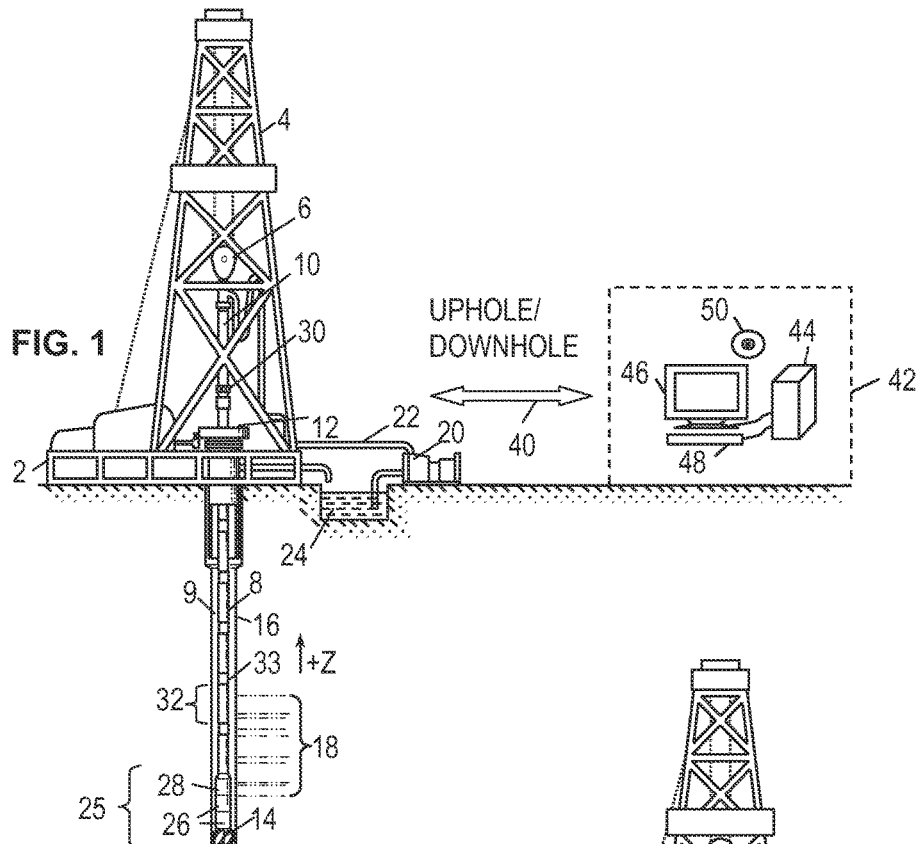
FIG. 1
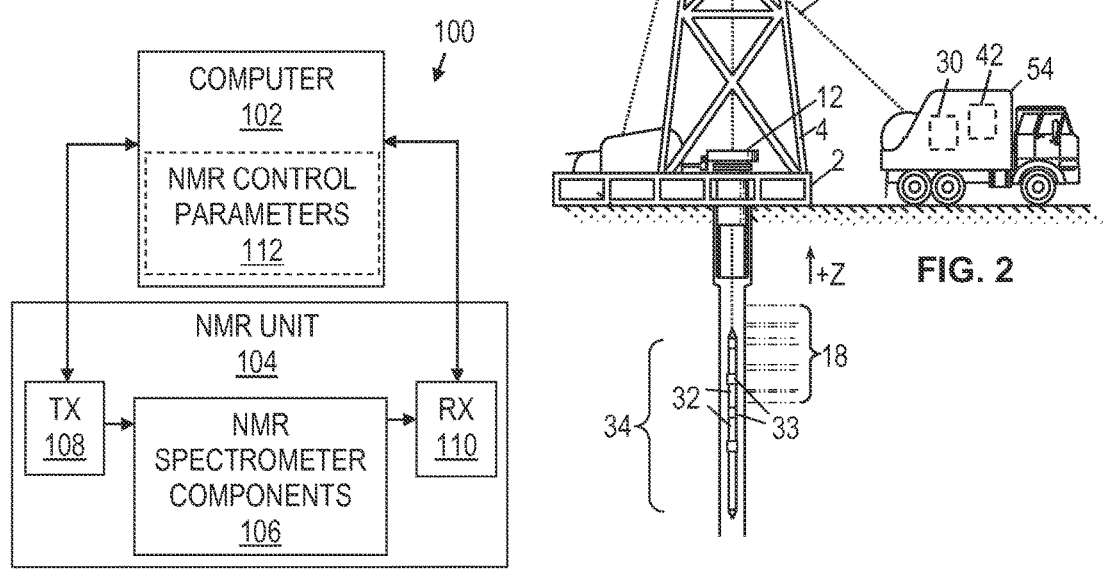
FIG. 3
FIG. 2

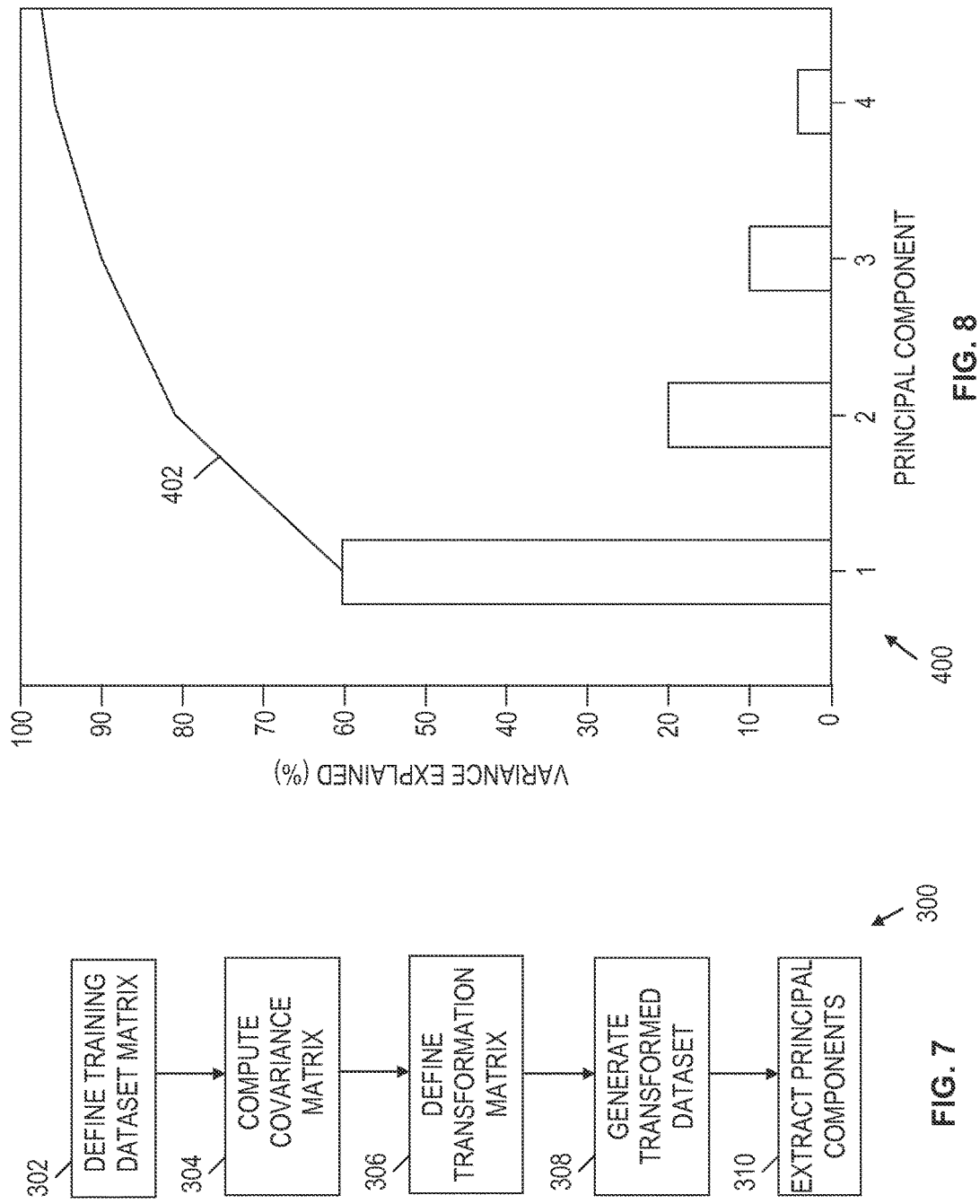

PREDICTING TOTAL ORGANIC CARBON (TOC) USING A RADIAL BASIS FUNCTION (RBF) MODEL AND NUCLEAR MAGNETIC RESONANCE (NMR) DATA

BACKGROUND

Understanding the reservoir fluids, hydrocarbon-generating potential, and formation characteristics of a reservoir rock formation is important to estimate the reserve and to improve the efficiency of oil field operations such as drilling, well completion, and production. To this end, various types of formation and reservoir analysis are performed using downhole tools. Further, various types of rock sample analysis are performed using laboratory tools at earth's surface. One example of formation or rock sample analysis involves nuclear magnetic resonance (NMR) phenomena.

An example NMR tool includes a magnet assembly that produces a static magnetic field ($B_0$), and a coil assembly that generates radio frequency (RF) electromagnetic signals (including a perturbing magnetic field ($B_1$)) and that detects magnetic resonance phenomena. The behavior of nuclei in presence of $B_0$ and $B_1$ has been correlated with formation rock and fluid properties such as the amount of hydrogen in pore space fluids and/or the porosity.

Total organic carbon (TOC) is an important reservoir quality indicator, particularly for unconventional source rock reservoirs. It is well-known that TOC can be obtained from laboratory mineralogy and fluid analysis using techniques such as the combination of X-ray diffraction (XRD) and X-ray fluorescence (XRF). However, laboratory tests are expensive and time consuming. Performing such tests for a large number of samples corresponding to a particular reservoir or even a single well is impractical. Nuclear logging based mineralogy analysis can also be used to estimate TOC, provided that all elements in the formation can be resolved, which is not always possible. Combining density and NMR logging measurements can also be used to estimate TOC, with an assumption that NMR logs do not include any signals from organic matters, liquid or solid, in the source rocks, an assumption not always valid.

BRIEF DESCRIPTION OF THE DRAWINGS

Accordingly, there are disclosed herein methods and systems to predict total organic carbon (TOC) values using a radial basis function (RBF) model and nuclear magnetic resonance (NMR) data. In the figures:

FIG. 1 is a schematic diagram showing an illustrative logging-while-drilling (LWD) survey environment.

FIG. 2 is a schematic diagram showing an illustrative wireline logging survey environment.

FIG. 3 is a block diagram showing an illustrative NMR system.

FIG. 7 is a diagram showing an illustrative principal component analysis (PCA) process.

FIG. 8 is a graph that shows illustrative data variance as a function of individual principal components.

Figure 4:
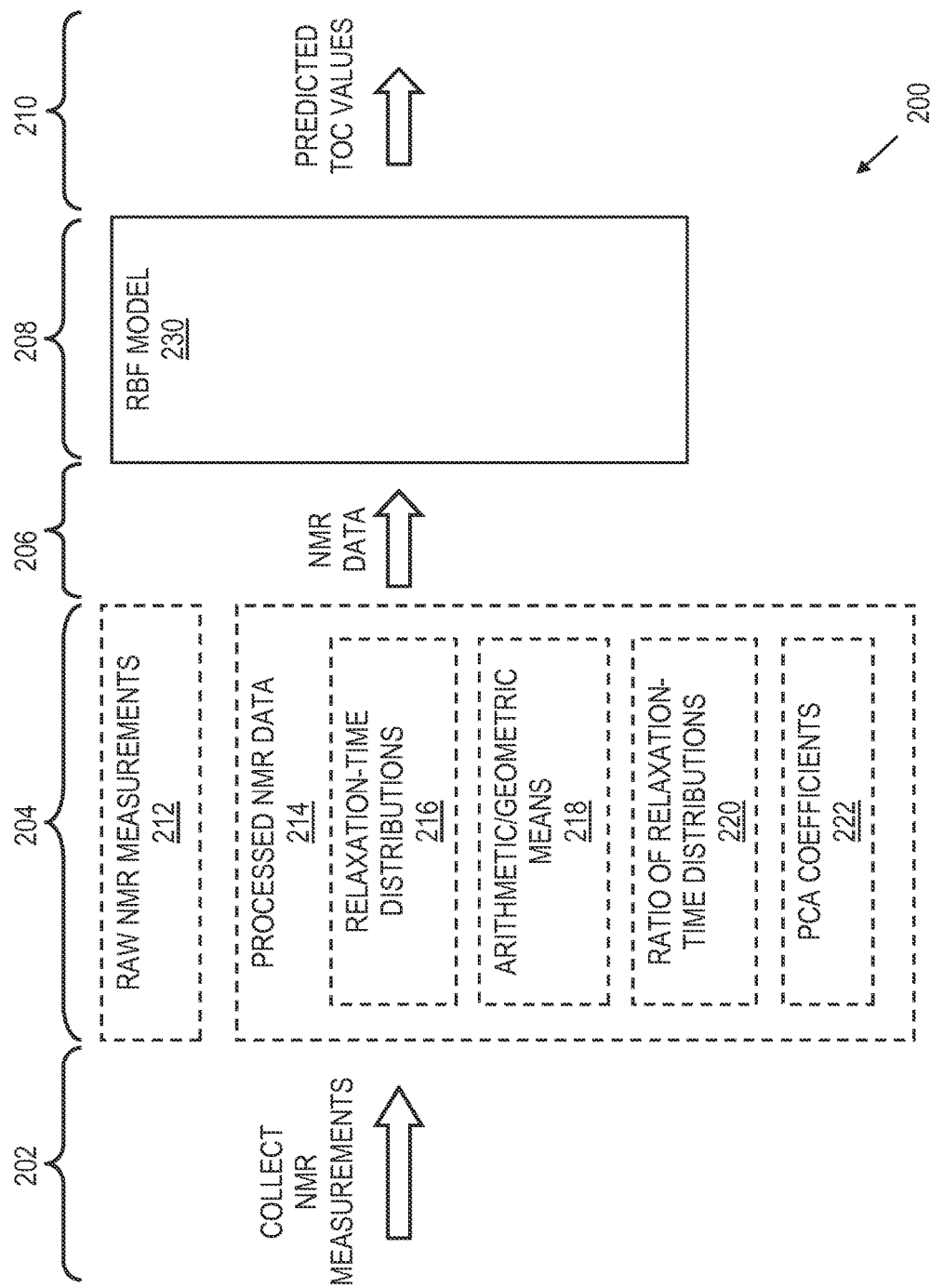
FIG. 4 is a block diagram showing an illustrative TOC prediction process.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Disclosed herein are methods and systems to predict total organic carbon (TOC) values using nuclear magnetic resonance (NMR) data applied to a radial basis function (RBF) model. As an example, predicted TOC values may be in the form of a log that plots TOC values as a function of measured depth. The RBF model used to predict TOC values may be trained using a variety of inputs such as principal components representing one or more NMR relaxation-time distributions, measured TOC data points of rock samples, gamma ray logging data, and clay bound water (CBW) values (e.g., derived from NMR relaxation-time distributions). Once trained, the RBF model predicts TOC values using, at least in part, NMR relaxation-time distributions derived from NMR measurements collected by a downhole logging tool or a laboratory tool. The predicted TOC values may be stored for later use and analysis, printed in a report, and/or displayed via a monitor.

In at least some embodiments, an example method includes obtaining NMR data and training an RBF model based on the NMR data and measured TOC values. The method also includes obtaining subsequent NMR data and employing the trained RBF model to predict TOC values based at least in part on the subsequent NMR data. The method also includes storing or displaying the predicted TOC values. Meanwhile, an example system includes at least one processor and a memory in communication with the at least one processor. The memory stores instructions that, when executed cause the at least one processor to obtain NMR data and to train an RBF model based on the NMR data and measured TOC values. The instructions, when executed, further cause the processor to obtain subsequent NMR data and to employ the trained RBF model predict TOC values based at least in part on the subsequent NMR data. The instructions, when executed, further cause the processor to store or display the predicted TOC values. In some cases, a previously trained RBF model may be obtained. In such case, the above method or system need not perform RBF model training. However, it should be appreciated that, as needed, a trained RBF model may be updated.

The disclosed methods and systems are compatible with various options. For example, the NMR data input to the RBF model to predict TOC values may include the time-domain NMR measurements such as Can Purcell Meiboom Gill (CPMG) echo decay, NMR relaxation-time distributions derived from NMR measurements, principal components representing NMR relaxation-time distributions derived from NMR measurements, an arithmetic or geometric means of an NMR relaxation-time distribution derived from NMR measurements, and/or a ratio of different NMR relaxation-time distributions (e.g., a $T_1/T_2$ distribution)

derived from NMR measurements. In addition to NMR data, natural gamma ray counts data or other available data may be input to the RBF model to predict TOC values. The RBF model used to predict TOC values may be trained using any of the above NMR data examples as well as measured TOC data points derived from measured TOC data points for a rock sample (e.g., obtained from laboratory test results). Further, the RBF model may be trained using gamma ray logging data, clay bound water (CBW) values, porosity values, or other data. In some embodiments, the data used for training is derived solely from available NMR data. Alternatively, at least some of the training data may be derived independent of available NMR data. Predicting TOC values may include selection or use of various data set options, RBF modeling options, and principal component analysis (PCA) options as described herein.

The disclosed methods and systems are best understood in an application context. Turning now to the figures, FIG. 1 shows an illustrative logging-while-drilling (LWD) environment. In FIG. 1, a drilling platform 2 is equipped with a derrick 4 that supports a hoist 6 for raising and lowering a drill string 8. The hoist 6 suspends a top drive 10 suitable for rotating the drill string 8 and lowering the drill string 8 through the well head 12. Connected to the lower end of the drill string 8 is a drill bit 14. As bit 14 rotates, it creates a borehole 16 that passes through various formations 18. A pump 20 circulates drilling fluid through a supply pipe 22 to top drive 10, down through the interior of drill string 8, through orifices in drill bit 14, back to the surface via the annulus 9 around drill string 8, and into a retention pit 24. The drilling fluid transports cuttings from the borehole 16 into the pit 24 and aids in maintaining the integrity of the borehole 16. Various materials can be used for drilling fluid, including oil-based fluids and water-based fluids.

In FIG. 1, logging tools 26 are integrated into a bottom-hole assembly 25 near the bit 14. As the bit 14 extends the borehole 16 through the formations 18, logging tools 26 collect measurements relating to various formation properties as well as the tool orientation and various other drilling conditions. Each of the logging tools 26 may take the form of a drill collar, i.e., a thick-walled tubular that provides weight and rigidity to aid the drilling process. For the present discussion, the logging tools 26 are expected to include an NMR logging tool that collects raw NMR measurements. The bottom-hole assembly 25 also may include a telemetry sub 28 to transfer raw NMR measurements or processed NMR data to a surface communication interface 30 and to receive commands from the surface. Example telemetry options include mud pulse telemetry, acoustic telemetry, electromagnetic telemetry, wired drill pipe telemetry, or a combination of telemetry options. The surface communication interface 30 forwards the raw NMR measurements or processed NMR data to and/or receives commands from a computer system 42 via a wired or wireless interface 40.

The computer system 42 may perform various operations such as providing commands for logging tools 26, storing raw NMR measurements or processed NMR data, further processing NMR measurements or NMR data, training an RBF model, employing a trained RBF model to predict TOC values as described herein, and displaying related information to an operator. As an example, in at least some embodiments, the computer system 42 includes a processing unit 44 that performs various operations by executing software or instructions obtained from a local or remote non-transitory computer-readable medium 50. The computer system 42 also may include input device(s) 48 (e.g., a keyboard, mouse, touchpad, etc.) and output device(s) 46 (e.g., a monitor, printer, etc.). Such input device(s) 48 and/or output device(s) 46 provide a user interface that enables an operator to interact with the logging tools 26 and/or software executed by the processing unit 44. For example, the computer system 42 may enable an operator to select NMR logging options, to view raw NMR measurements, to view processed NMR data, to adjust RBF model training options, to adjust training data sets, to adjust inputs to a trained RBF model, to adjust PCA options, and/or to perform other tasks.

In different embodiments, an NMR logging tool corresponding to logging tool 26 may include processing, storage, and/or other components to select pulse sequences, to store echo information (e.g., amplitude as a function of time), to calculate parameters derived from the stored echo information (e.g., a $T_1$ distribution, a $T_2$ distribution, a diffusion measurement, and/or a porosity), to update NMR logging operations based on the calculated parameters and/or to update NMR logging operations in response to commands from the surface. Such commands from the surface may be generated in response to programmed logging operations performed by computer system 42, parameters derived from collected echoes by computer system 42 or operator, and/or an operator otherwise selecting or entering logging control options via a user interface.

At various times during the drilling process, the drill string 8 may be removed from the borehole 16 as shown in FIG. 2. Once the drill string has been removed, logging operations can be conducted using a logging string (sonde) 34 suspended by a cable (wireline) 52 having conductors for transporting power to the logging string 34 and telemetry from the logging string 34 to the surface. In some embodiments, the logging string 34 may have pads and/or centralizing members to maintain logging tools 32 near the axis of the borehole as the logging string 34 is pulled uphole. The logging tools 32 may correspond to a variety of logging tools including an NMR logging tool with the same or similar features as the NMR logging tool described for logging tool 26. A logging facility 54 includes a surface communication interface 30 and a computer system 42 for receiving, storing, and processing raw NMR measurements or processed NMR data obtained by the logging tools 32. The computer system 42 of FIG. 2 may also send commands and/or logging control parameters to the logging tools 32, perform RBF model training, predict TOC values, and/or perform other operations as described herein.

Although the disclosed method and systems are directed to obtaining NMR data and employing an RBF model to predict TOC values based on the obtained NMR data, it should be appreciated that other logging data may be collected and applied to an RBF model to predict TOC values. For example, in some embodiments, gamma ray data in addition to NMR data is collected and applied to an RBF model to predict TOC values. In such case, the logging tools 26 of FIG. 1 and the logging tools 32 of FIG. 2 may include a gamma ray logging tool as well as an NMR logging tool. Additionally or alternatively, other logging tools and corresponding measurements/logs may be used along with NMR data to predict TOC values.

FIG. 3 shows a block diagram of an illustrative NMR system 100. As shown, the NMR system 100 includes a computer 102 that provides NMR control parameters 112 to an NMR unit 104. In different embodiments, the components of NMR system 100 may be located at earth's surface (e.g., as part of an NMR facility or laboratory) or downhole (e.g., as part of logging tools 26 or 32). Alternatively, some of the components (e.g., computer 102) may be located at earth's surface while other components (e.g., NMR unit 104) are located downhole. Regardless of component location, the computer 102 directs the operations of the NMR unit 104 (e.g., a downhole tool or laboratory equipment), which includes a transmitter (TX) 108, a receiver (RX) 110, and NMR spectrometer components 106.

More specifically, the computer 302 is configured to provide commands, programming, and/or data to transmitter 108 of the magnetic resonance unit 104. The transmitter 108 may include a programmable pulse sequence device or storage, a radio frequency (RF) synthesizer, a phase shifter, a pulse gate, an amplifier, and/or other components. Further, in different embodiments, the magnetic resonance control parameters 112 enable adjustment of pulse sequences and receiver window options based on a default configuration, user selection, and/or calibration.

The magnetic resonance unit 104 also includes magnetic resonance spectrometer components 106 used for magnetic resonance operations. Examples of magnetic resonance spectrometer components 106 include one or more magnets, shim coils, probes/antennas, and/or field-frequency lock components. Further, the magnetic resonance spectrometer components 106 may include a duplexer that enables separation between transmission current and reception current. The receiver 110 of magnetic resonance unit 104 is configured to receive and decode magnetic resonance signals. The receiver 110 may include, for example, an analog-to-digital converter (ADC), filters, mixers, splitters, pre-amplifiers, and/or other components to receive magnetic resonance signals and recover measurement data. The raw NMR measurements or processed NMR data is output from the receiver 110 to computer 102 for storage, display, and/or analysis. In some embodiments, the computer 102 may further process raw NMR measurements or processed NMR data received from the NMR unit 104. Further, the computer 102 may predict TOC values as described herein, or may forward raw NMR measurements and/or processed NMR data to another computer that predicts TOC values as described herein.

FIG. 4 is a block diagram of an illustrative TOC prediction process 200. As shown, the process 200 includes collecting NMR measurements at stage 202. As previously discussed, the NMR measurements may be collected by a LWD tool, a wireline tool, and/or an NMR laboratory tool. In at least some embodiments, the NMR measurements are collected at stage 202 by energizing and manipulating nuclear spins in a formation with a pulsed radio frequency (RF) magnetic field. Various pulse sequences (i.e., series of RF pulses, delays, and other operations) can be used to collect the NMR measurements. Example pulse sequences include the CPMG sequence (in which the spins are first flipped to the plane perpendicular to the static magnetic field direction using a tipping pulse followed by a series of refocusing pulses), the Optimized Refocusing Pulse Sequence (ORPS) in which the refocusing pulses are less than 180°, a saturation recovery pulse sequence, and other pulse sequences.

At stage 204, the NMR measurements collected at stage 202 are conveyed as raw NMR measurements 212 and/or are processed. Examples of processed NMR data 214 include relaxation-time distributions 216 (e.g., $T_1$ or $T_2$ distributions), arithmetic or geometric means 218 (e.g., arithmetic or geometric means of $T_1$ or $T_2$ distributions), ratio of relaxation-time distributions 220 (e.g., $T_1/T_2$), and PCA coefficients 222 (e.g., PCA coefficients for $T_1$ or $T_2$ distributions). The processed NMR data 214 represented in stage 204 may be derived by the same computer that predicts TOC values using a RBF model or by at least one other processing component (e.g., in a downhole logging tool, a laboratory computer, or another computer) that handles the NMR measurements collected at stage 202.

As an example of processing NMR measurements, NMR measurements collected at stage 202 may correspond to a spin-echo train that includes a series of multi-exponential decays. In such case, relaxation-time distributions represent a discrete population density of the decay rates extracted from the spin-echo train. More specifically, such NMR measurements can be described as multiple components resulting from multiple different relaxation times in the measured region. For example, the signal amplitude of the first echo may be expressed approximately by:

$$\phi(t = TE) = \sum_{i=1}^{N} \phi_i(TE),$$

where $$\phi_i(t) = c_i \exp\left(-\frac{t}{T_{2i}}\right).$$

Here, each of the N components has a respective amplitude of $\phi_i$ and a characteristic relaxation time $T_{2i}$.

In some source rocks, some of the components (i<k) (those having the shortest relaxation times $T_{2i}$) decay too quickly to produce a measurable signal at t=TE. In such case, the measurable signal amplitude is the apparent porosity:

$$\phi_{app}(TE) = \sum_{i=k}^{N} \phi_i,$$

which is smaller than the total signal (total porosity):

$$\phi = \sum_{i=1}^{N} \phi_i.$$

The $T_2$ distribution derived from the NMR measurement can then be described as: $\phi$: $\{\phi_i$ vs. $T_{2i}$, where i=k: N and $\phi_i$=0 for i<k$\}$. Clearly, it is desirable to set the interecho time TE as short as possible in data acquisition, in order to be able to measure the short relaxation time components. However, the minimum TE is generally constrained by the hardware, available power, and operating frequency. Thus, the apparent porosity is still in deficit compared to the total porosity. This porosity deficit is, in general, not detrimental to the use of the method disclosed herein, as long as the RBF model is generated with NMR data having similar characteristics. Thus, in accordance with at least some embodiments, the NMR training data is acquired with substantially the same TE as that used in logging data acquisition. On the other hand, the difference between the NMR apparent porosity and the true total porosity can be used to aid the TOC computation, as the missing porosity may represent solid organic matters that are part of TOC. For example, an independent porosity measurement, such as a porosity derived from density logging measurement, can be used an additional input to train the RBF model and to obtain TOC predictions from the RBF model. This use of density and NMR information is different from the method described in U.S. Pat. App. Pub. No. 20090254283 A1 by Jacobi, et al., as the latter assumed that all TOC components are not measured by NMR, while the disclosed embodiments have no such limitation.

At stage 206, NMR data representing the raw NMR measurements 212 and/or at least some of the processed NMR data 214 is forwarded to an RBF model 230 at stage 208. In at least some embodiments, the RBF model 230 outputs predicted TOC values represented at stage 210. The predicted TOC values of stage 210 may be stored or displayed. In accordance with at least some embodiments, the predicted TOC values represented at stage 210 can be obtained by training the RBF model 230 using a limited amount of measured TOC data points and available NMR data. The measured TOC data points may be obtained from laboratory test results. As desired, the measured TOC data points may be resolution-matched relative to the available NMR data used for training the RBF model.

Figure 5:
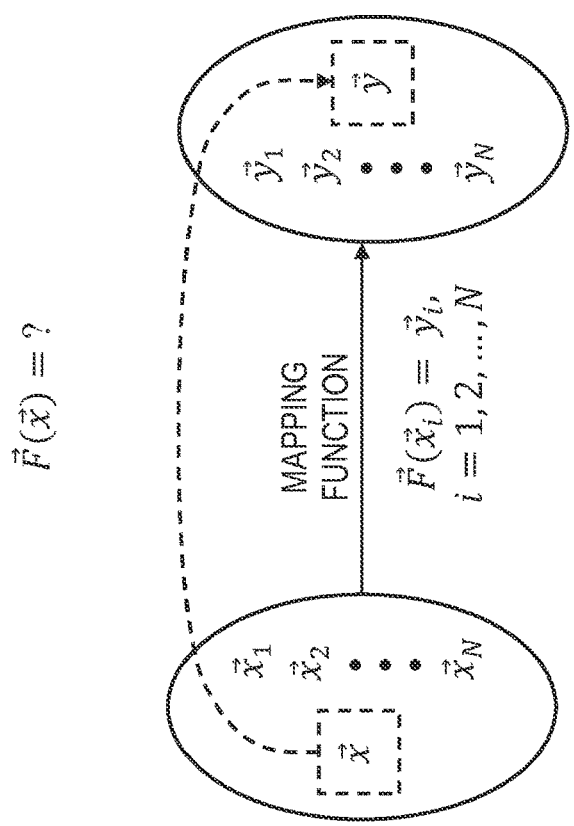
FIG. 5 is a diagram showing an illustrative mapping function.

In accordance with at least some embodiments, the RBF model 230 is created using the NMR data of stage 206 by solving one or more inverse problems. Inverse problems encountered in well logging and geophysical applications may involve predicting the physical properties of some underlying system given an input data set. Referring to FIG. 5, consider a database having a set of distinct input data $\vec{x}_i \in R^n$ (i.e., the inputs are n-dimensional vectors) and a set of corresponding outputs, $\vec{y}_i \in R^m$, for i=1, ..., N, where N is the number of cases in the database. The different cases in the database represent different states of the underlying physical system. In this notation, $\vec{y}_i$ values represent samples of the function that one wants to approximate (e.g., by a model), and $\vec{x}_i$ values are the distinct points at which the function is given. The database is used to construct a mapping function such that, $\vec{F}(\vec{x}_i) = \vec{y}_i$, for i=1, ..., N. As used herein, the mapping function can be solved through the inverse problem of predicting TOC values for a formation based on available NMR data.

Figure 6:
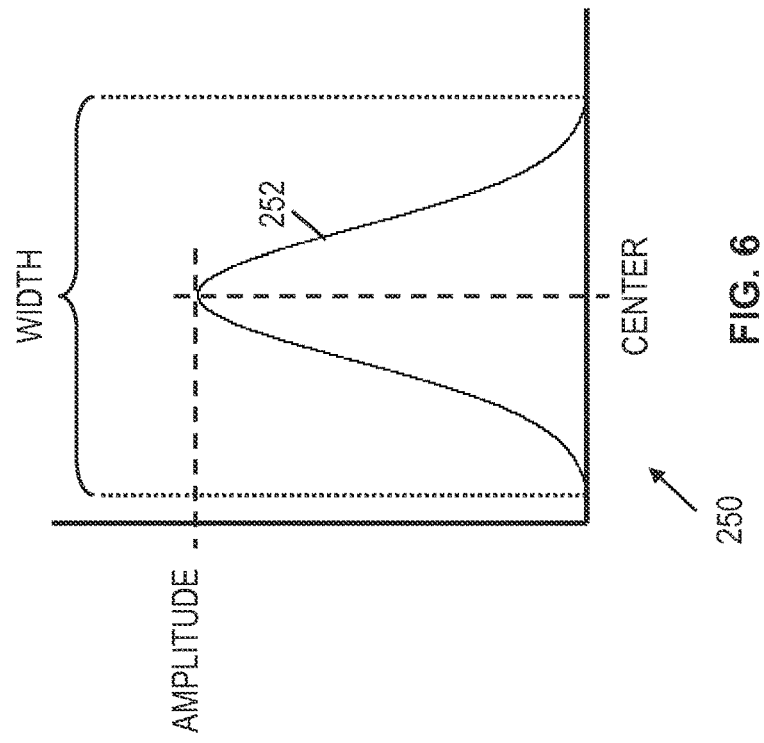
FIG. 6 is a graph showing an illustrative function used for RBF modeling.

In at least some embodiments, the RBF model 230 corresponds to a TOC prediction model constructed from RBFs. Further, PCA may be applied to preprocess at least some of the data used to train the RBF model 230. FIG. 6 shows an illustrative RBF from which RBF model 230 may be constructed. In graph 250 of FIG. 6, the RBF corresponds to a Gaussian function having a given center, amplitude, and width. To concept of constructing an RBF model such as RBF model 230 involves combining multiple basis functions having different characteristic parameters (e.g., center, amplitude, width, and sign) according to a set of predetermined rules. It should be appreciated that basis functions other than Gaussian functions may be used to construct an RBF model. Further, it should be appreciated that the rules for combining multiple basis functions to construct an RBF model may be adjusted. Such rules may include the number of basis functions to be used, characteristic parameter maximums, characteristic parameter minimums, characteristic parameter ranges, data normalization options, data fit options, etc. Various details for constructing an RBF model from basis functions are discussed later.

Typically, the NMR measurements represented in stage 202 are affected by noise, and the noise is introduced into the processed NMR data 214 derived from the NMR measurements. In some instances, important structures of the processed NMR data 214 are less affected by the noise, and these important structures can be used for training the RBF model 230. In addition, data within different types of processed NMR data 214 are often highly correlated, and thus contain redundancies that can unnecessarily increase the complexity of the RBF model 230. To account for these phenomena, PCA operations may be performed to reduce processed NMR data 214 (e.g., relaxation-time distributions) to a subset of key components. In at some embodiments, PCA operations provide a rank ordering of variances in at least some of the processed NMR data 214. The rank ordering can be structured such that principal components with larger associated variances represent important structure (signal), while those with lower variances represent noise or insignificant information.

Such PCA operations can be described as transforming a set of data vectors from an initial coordinate system to a new coordinate system. The new coordinate system can be defined such that when the data vectors are expressed in the new coordinate system all (or substantially all) significant variations among the data vectors are described by a reduced number of vector components. Thus, although the data vectors may have the same number of components in both coordinate systems, most of the vector components in the new coordinate system can be ignored or neglected; the retained vector components form a set of principal components that are used to analyze the data.

In some cases, the $k^{th}$ principal component is the $k^{th}$ component of a transformed data vector in the new coordinate system. The proportion of the total variance accounted for by the $k^{th}$ principal component can be:

$$\frac{\lambda_k}{\sum_{i=1}^{n} \lambda_i},$$

where $\lambda_i$, i=1, ..., n are the eigenvalues of the covariance matrix of the training data set. Each of the eigenvalues quantifies the variance of the corresponding principal component.

Referring to FIG. 7, an example PCA process 300 can be used to generate sets of principal components from relaxation-time distributions, where each set of principal components represents a respective one of the relaxation-time distributions. The process 300 can include additional or different operations, and the operation can be performed in the order shown or in another order.

At block 302, a dataset matrix X is formed from the relaxation-time distributions. Each of the n relaxation-time distributions has p elements, so the dataset matrix X can be an n×p matrix (n rows, p columns), in which each of the relaxation-time distributions forms a respective row. The training dataset of relaxation-time distributions can be represented in another manner, using any suitable data format, data structure, or data type.

The relaxation-time distributions can include distributions of transverse relaxation times or longitudinal relaxation times obtained from NMR data. In some cases, the area integration of each distribution is normalized to a common normalizing value. For example, the normalizing value can be 1 or another constant value. To normalize a distribution, the values in the distribution can be multiplied or scaled uniformly so that the area of the scaled distribution is equal to the normalizing value.

At block 304, the eigenvectors of the covariance matrix C of dataset matrix X are determined. The covariance matrix C may be computed as $C=X^T X$, where $X^T$ is the transpose of the dataset matrix X, or the covariance matrix can be computed in another manner. In some instances, one or more of the eigenvectors can be obtained without explicitly computing the covariance matrix.

At block 306, a transformation matrix $W_L$ is formed, where $W_L$ is a p×l matrix whose columns are eigenvectors of the covariance matrix C. The transformation matrix $W_L$ can be formed from the l eigenvectors that correspond to the l largest eigenvalues of the covariance matrix C. The eigenvectors and eigenvalues of the covariance matrix C can be determined, for example, by conventional techniques for computing matrix eigenvectors and eigenvalues.

At block 308, the dataset matrix X is converted to a new coordinate system, resulting in a transformed matrix $T=XW_L$. At block 310, sets of principal components are extracted from the transformed matrix T. In at least some embodiments, the transformed matrix T is an n×l matrix, and the $i^{th}$ row contains a set of principal components corresponding to the $i^{th}$ relaxation-time distribution in the dataset matrix X. For example, the matrix element T(i,k) (the element at the $k^{th}$ column and $i^{th}$ row) can represent the $k^{th}$ principal components of the $i^{th}$ relaxation-time distribution.

In some embodiments, the data vectors (in the initial coordinate system) can be the $T_2$ distributions of a database corresponding to NMR measurements or related NMR data, and each data vector can have 27 or 54 components. In some cases, the relaxation-time bins are evenly spaced along the logarithmically-scaled axis; or the bins may be spaced in another manner. After the data vectors are transformed to the new coordinate system, the first few principal components (i.e., the first few components of the transformed data vectors) are retained for use in training (or using) the RBF model 230. The other components can be disregarded because they primarily represent noise, insignificant variations, or redundancy.

Referring to FIG. 8, plot 400 shows that for an example database of $T_2$ distributions, the first three principal components (labeled 1, 2, 3) account for over 90% of the variances. The curve 402 in the plot 400 shows the cumulative variance after each additional principal component is added. With the understanding that lower variances are more likely to represent noise or redundancy, the components having lower variances can be discarded. In some embodiments, the number of retained components is determined by comparing the ratio:

$$\frac{\sum_{i=p+1}^{n} \lambda_i}{\sum_{i=1}^{n} \lambda_i}$$

with noise-to-signal ratio:

$$\frac{\sigma_{noise}^2}{\sigma_{signal}^2}$$

in the NMR measurement data, where p is the number of retained components. For example, in some embodiments, processed NMR data corresponds to stacked data such that the noise level is below a threshold (e.g., 1 p.u.). Assuming the average porosity is around 30 p.u., the noise-to-signal ratio is about 3 percent. In this example, three principal components of the $T_2$ distribution may be retained. However, it should be appreciated that a greater number of principal components can be retained for use in training or using the RBF model. For example, in some embodiments, four, five, six, or more principal components are retained.

Figure 9:
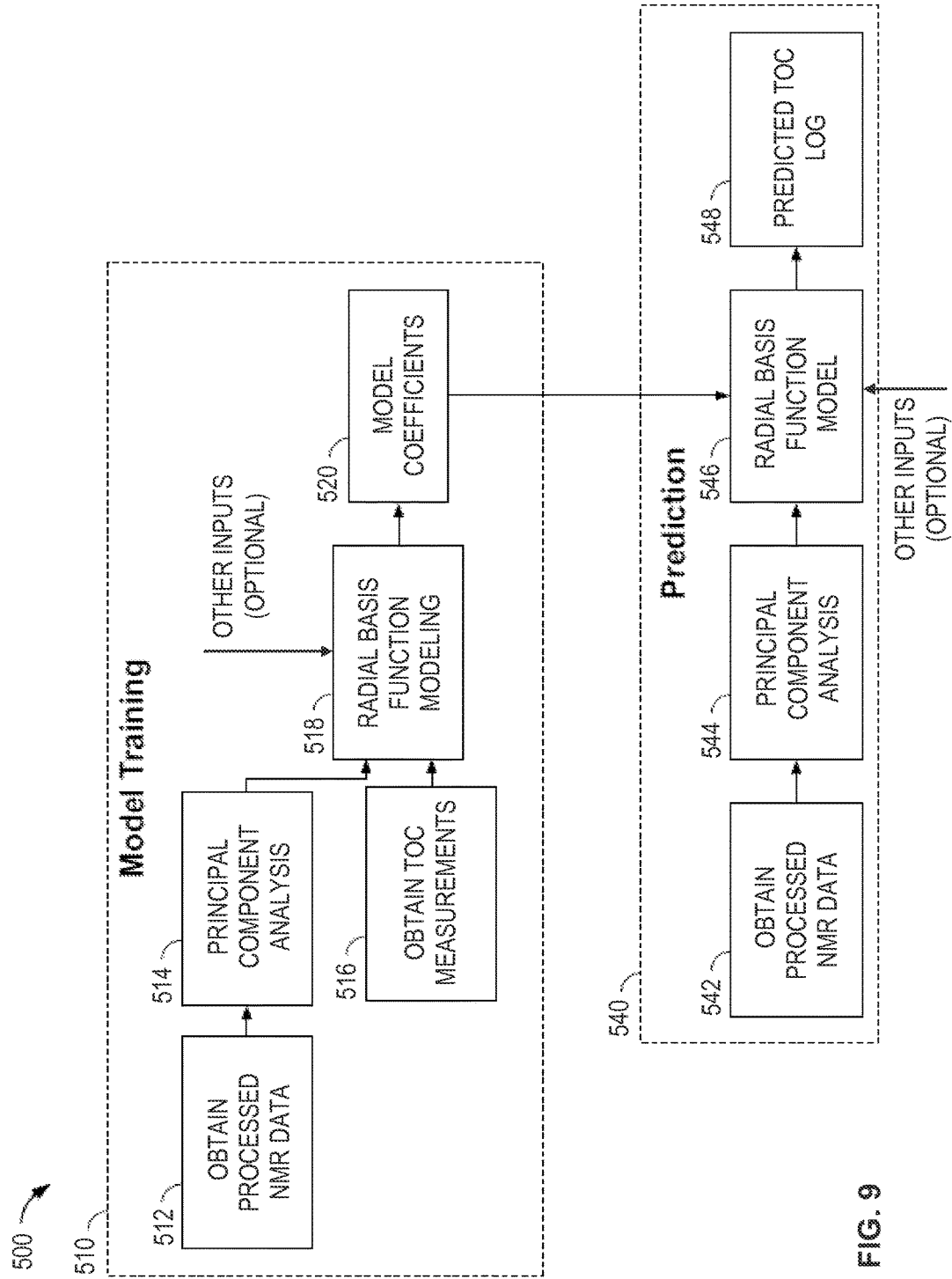
FIG. 9 is a block diagram showing an illustrative process for training and using an RBF model to predict TOC values.

An example process 500 for predicting TOC values from NMR measurements is shown in FIG. 9. The process 500 shown in FIG. 9 includes a model training phase 510 and TOC prediction phase 540. The model training phase 510 can be used to develop a mapping function based on a database of NMR measurements or processed NMR data, and measured TOC values (e.g., TOC values or curves obtained from laboratory tests). Meanwhile, the TOC prediction phase 540 can be used to predict TOC values based on NMR measurements or processed NMR data and the developed mapping function. The process 500 can include additional or different steps, and the steps can be configured as shown or in another manner.

In at least some embodiments, the model training phase 510 includes obtaining processed NMR data at block 512. The processed NMR data obtained at block 512 may correspond to relaxation-time distributions or other processed NMR data derived from NMR measurements collected by a downhole NMR logging tool or a laboratory NMR tool. The processed NMR data obtained at block 512 becomes part of a training database. At block 514, the training database of relaxation-time distributions or other processed NMR data can be reduced to a subset of key components (i.e., the "principal" components of the database) through PCA operations. Further, measured TOC values are obtained at block 516 for a particular rock sample of interest. As an example, the measured TOC values obtained at block 516 may correspond to TOC values measured using X-ray diffraction (XRD), X-ray fluorescence (XRF), or other laboratory tests on a rock sample. For the purposes of model training, these measured TOC values can be treated as "ground truth" values, and can be used to determine correlations between NMR measurements or processed NMR data and at least some of the measured TOC values.

The principal components of the training database obtained at block 514 and the measured TOC values obtained at block 516 are used to train an RBF model (e.g., RBF model 230) at modeling block 518. In at least some embodiments, an RBF is a function in the form of $\varphi(\|\vec{x}-\vec{x}_c\|)$, where $\|\vec{x}-\vec{x}_c\|$ is the Euclidean distance between the points $\vec{x}$ and $\vec{x}_c$ and where $\vec{x}$ is the variable and $\vec{x}_c$ is the center of the radial basis function. An RBF model $F(\vec{x})$ can be represented as a linear combination of RBFs. The RBF model can be used to approximate the physical system $f(\vec{x})$ to a certain degree of accuracy, for example, assuming the underlying physical system $f(\vec{x})$ is smooth and continuous.

In at least some embodiments, an RBF model $F(\vec{x})$ is derived at modeling block 518 by interpolating an input-output data set $\{(\vec{x}_i, \vec{y}_i)\}_{i=1}^{N}$ sampled from an underlying physical system $f(\vec{x})$, where $\{\vec{x}_i\}_{i=1}^{N}$ is the database of relaxation-time distributions transformed by PCA analysis, and $\{\vec{y}_i\}_{i=1}^{N}$ are the measured TOC values corresponding to available NMR data. An RBF model can be represented $$F(\vec{x}) = \sum_{i=1}^{N} \vec{w}_i \varphi(\|\vec{x} - \vec{c}_i\|).$$

where, $F(\vec{x}_i) = \vec{y}_i$, $i = 1, 2, \ldots, N$,

In this example model, $\{\vec{w}_i \varphi(\|\vec{x} - \vec{c}_i\|)\}_{i=1}^{N}$ is a set of weighted radial basis functions, N, $\vec{w}_i$, and $\vec{c}_i$ are model coefficients, and $\{(\vec{x}_i, \vec{y}_i)\}_{i=1}^{N}$ is the input-output training set.

In the above model, the parameters $\{(\vec{c}_i)\}_{i=1}^{N}$ represent the centers of the RBF model. In some embodiments, the centers correspond to input training parameters obtained from a database of relaxation-time distributions transformed by PCA analysis, principal components of normalized relaxation-time distributions, corresponding to total porosities, or combinations of these and other input training parameters. In this case, the RBF model can be represented as:

$$F(\vec{x}) = \sum_{i=1}^{N} \vec{w}_i \varphi(\|\vec{x} - \vec{x}_i\|),$$

where N, $\vec{w}_i$, and $\vec{x}_i$ are the model coefficients. The function $\varphi$ can be a Gaussian function or another type of smooth function. For example, when the function $\varphi$ is a Gaussian, the matrix associated with the interpolation is well-conditioned, and the RBF inversion has a unique solution.

In at least some embodiments, other inputs are optionally provided to modeling block 518. Examples of other inputs that may be used to train an RBF model include gamma ray log data and clay bound water (CBW) data. The training operations performed at modeling block 518 generates, for example, model coefficients 520, where the resulting RBF model and its coefficients can be used as a mapping function that predicts TOC values based on subsequent NMR data.

In at least some embodiments, the model coefficients 520 obtained by modeling block 518 can be determined by interpolation of available training datasets. In some instances, the coefficients $\vec{w}_i$ can be determined by requiring that the interpolation equations be satisfied exactly. For example, the coefficients can be a linear combination of the function values $$\vec{w}_i = \sum_{j=1}^{N} \Phi_{ij}^{-1} \vec{y}_j,$$

where $\Phi_{ij}^{-1}$ is the (i,j) element of the inverse of the N×N interpolation matrix In accordance with at least some embodiments, the RBF model and model coefficients can be used to predict TOC values based on processed NMR data such as an input relaxation-time distribution. An input relaxation-time distribution can be obtained from available NMR measurements, for example, using NMR signal inversion. In some embodiments, the NMR data used to predict TOC values is obtained independently from NMR data used to train the RBF model. For example, the NMR data used to predict TOC values may correspond to a subterranean formation with unknown TOC values.

In at least some embodiments, the process of predicting TOC values involves remapping a relaxation-time distribution or other processed NMR data corresponding to a subterranean formation with unknown TOC values to a new coordinate system identified during RBF model training. That is, the dataset matrix $X_{input}$ can be transformed to the new coordinate system by the operation $T_{input} = X_{input} W_L$, where the transformed matrix $T_{input}$ has l columns. Here, each element $T_{input}(i,k)$ (the element at the $k^{th}$ column, $i^{th}$ row) represents the $k^{th}$ principal component of the $i^{th}$ input relaxation-time distribution, and $W_L$ represents the transformation matrix identified during model training.

Transformed matrix $T_{input}$ can be input into the RBF model, using the model coefficients identified during model training. That is, if $T_{input}$ represents the vector elements of $\vec{x}$, the predicted TOC values $F(\vec{x})$ can be determined by:

$$F(\vec{x}) = \sum_{i=1}^{N} \vec{w}_i \varphi(\|\vec{x} - \vec{c}_i\|),$$

where N, $\vec{w}_i$, and $\vec{c}_i$ are the model coefficients identified during model training. Thus, after model training, subsequent TOC values can be predicted using independently acquired NMR measurements.

In at least some embodiments, the TOC prediction phase 540 includes obtaining processed NMR data at block 542. The processed NMR data obtained at block 542 may correspond to relaxation-time distributions or other processed NMR data derived from NMR measurements collected by a downhole NMR logging tool or a laboratory NMR tool. At block 544, PCA is performed to determine the principal components for the processed NMR data. As an example, the principal components at block 544 may be determined based on principal component analysis results obtained at block 514 of the model training phase 510. The principal components determined at block 544 can then be used as an input to an RBF model at prediction block 546. At prediction block 546, the RBF model may also receive model coefficients identified at block 520 of the model training phase 510. In at least some embodiments, other inputs are optionally provided to prediction block 546. Examples of other inputs that may be used to predict TOC values using the RBF model of prediction block 546 include gamma ray log data and clay bound water (CBW) data. Further, it should be appreciated that different types of processed NMR data may be input to the RBF model of prediction block 546. Examples of processed NMR data include raw NMR measurements, NMR relaxation-time distributions derived from NMR measurements, a PCA data set representing NMR relaxation-time distributions derived from NMR measurements, an arithmetic or geometric means of an NMR relaxation-time distribution derived from NMR measurements, and a ratio of different NMR relaxation-time distributions (e.g., a $T_1/T_2$ distribution) derived from NMR measurements. At block 548, predicted TOC values (e.g., a predicted TOC log) are output from the prediction block 546.

In at least some embodiments, the predicted TOC values can be compared to the measured TOC values using a "leave one out" method, in which a sample from the training data set is taken out and its TOC is predicted using the RBF model developed with the rest of the data in the training data set. If predicted TOC value are within a predetermined threshold (e.g., within order of magnitude of the measured TOC values), the predicted TOC values may be considered to be acceptable.

Though more training samples may improve the RBF model used in prediction block 546 in some cases, using more samples as the centers in the RBF model does not necessarily result in better prediction performance in all cases. For instance, in some embodiments, increasing the number of centers in a RBF model may result in an RBF model that over-fits the available training data. Such over-fitting can negatively affect the prediction performance of the RBF model. In different embodiments, the number of samples used for the RBF centers can be selected empirically, or according to other selection criteria. In some cases, all the available training samples are used during the training process, including some instances where forward selection is used to select the centers.

In at least some embodiments, relaxation-time distributions or other processed NMR data used for RBF model training or TOC predictions can be normalized. For instance, in some embodiments, relaxation-time distributions can be separated into two parts: the relative shape of the distributions and the summation of the amplitudes of the distributions (i.e., the total porosities). Further, PCA can be applied to the relative shape of the distributions. For the above relaxation-time distributions, the resulting RBF model or TOC predictions would be dependent on the relative shape of the distributions and the summation of the amplitudes of the distributions. Example normalization values include 0.5, 1.0, 1.5, 2, 2.5, and so forth.

In at least some embodiments, the RBF model described herein corresponds to an interpolation method, where RBF model performance depends on the quality of the training database. For example, if the measured TOC values of the training database are very noisy and/or if too many centers are used for the interpolation, the RBF model can become overly sensitive to the details of the data, which may result in oscillatory behavior due to over-fitting. These detrimental effects can be mitigated in various ways.

For instance, in order to mitigate the effects of over-fitting, in some embodiments, the RBF model can be regularized according to a cost function that penalizes oscillatory behavior. The input data with noise can be described by:

$$F(\vec{x}_i) = \vec{y}_i + \varepsilon_i, \ i=1, 2, \ldots, N,$$

where $$F(\vec{x}) = \sum_{i=1}^{N} \vec{w}_i \varphi(\|\vec{x} - \vec{x}_i\|),$$

assuming the centers of the RBF functions are the set of training inputs, and $\varepsilon_i$ is the noise in the measurement data. The RBF model can be obtained by minimizing the following cost function:

$$E(F) = \sum_{i=1}^{N} (\vec{F}(\vec{x}_i) - \vec{y}_i)^2 + \lambda \sum_{i=1}^{N} \vec{w}_i^2,$$

where $$\sum_{i=1}^{N} (\vec{F}(\vec{x}_i) - \vec{y}_i)^2$$

is the fitting error, and $$\sum_{i=1}^{N} (\vec{w})_i^2$$

is the regularization term to penalize the oscillations in the fitting. The parameter $\lambda$ controls the balance between fitting the data and avoiding the penalty, and can be assigned different values depending on the desired fitting behavior. In some embodiments, the value of parameter $\lambda$ can be determined using generalized cross-validation methods in order to assess the accuracy of the resulting RBF model. Example cross-validation methods include K-fold cross validation, repeated random sub-sampling validation, and leave-one-out cross-validation. Use of regularization for an RBF model decreases the likelihood of over-fitting and susceptibility to noise in the training database compared to a non-regularized RBF model.

In at least some embodiments, in order to mitigate the effects of over-fitting, the centers of RBF model can be derived from only a subset of available relaxation-time distributions or other processed NMR data in a training database. That is, instead of using all the data of the training database for the centers of the RBF model, only a subset of the data set is selected for the centers of the RBF model. For example, in some embodiments, the goal of this selection is to find a subset which can explain most, but not all, of the variation in the training set, with the goal of avoiding over-fitting noise. In some instances, a subset of the training samples are used for the centers of the RBF model, and all the training samples (including the subset) are used to compute other parameters (e.g., the weights) of the RBF model.

An optimal or otherwise acceptable subset of training data used for the centers of the RBF model can be selected using various techniques. For instance, in the forward selection technique, individual centers can be added to the model one at a time, and each center can be tested for inclusion in the model. The most significant of these centers can then be added to the model.

An example embodiment of forward selection can be performed, where C is the collection of the centers of the RBF model, C1 is the collection of data which are candidates of the centers of the RBF model, and where initially C is empty and C1 is the training database. For each sample center in the collection C1, an RBF model can be constructed whose centers are the selected samples from C1 and the samples in the collection C. A sample center with the smallest SSE (i.e., is the sum of squared errors over all the sample centers in the training data set) is removed from C1 and added into C. This can be repeated, for example, until C1 is empty, or certain stop criteria is met.

There are several criteria which can be used to stop the selection process. For instance, the number of selected centers can be selected in order to minimize criteria such as the Bayesian information criterion (BIC), or the generalized cross-validation (CGV) criterion. For example, in a non-regularized RBF model, a CGV criterion can be represented as $$GCV = \frac{N}{(N-M)^2} SSE,$$

where N is the number of sample centers in the training database and M is the number of centers in the RBF model. In another example, in a non-regularized RBF model, a BIC can be represented as $$BIC = \frac{N + (\ln(N) - 1)M}{N(N-M)} SSE.$$

Accordingly, in some embodiments, the numbers of centers that minimize the GCV and/or BIC values may be selected for the RBF model. Use of forward selection for an RBF model decreases the likelihood of over-fitting and susceptibility to noise in the training database compared to an RBF model without forward selection. In some embodiments, backward selection can be used instead of forward selection. As an example, for an RBF model whose centers are made of all the samples in the training database, individual centers can be removed from the model one at a time, and each center can be tested for subtraction from the model.

In at least some embodiments, multiple techniques can be simultaneously used to reduce over-fitting. For example, in some embodiments, regularization is applied at each step of the forward selection method. In another example, in order to reduce computation requirements, regularization is applied to the RBF model after centers are selected using forward selection. Use of multiple techniques together decreases the likelihood of over-fitting and susceptibility to noise in the training database compared to an RBF model that does not use multiple techniques.

In some embodiments, the spatial resolution of measured TOC values differs from the spatial resolution of available NMR data. Generally, the available NMR data can have higher, lower or the same resolution as measured TOC values. In some embodiments, the measured TOC values have a relatively higher vertical resolution, while the available NMR data has a relatively lower vertical resolution. For example, the vertical resolution of available NMR data may be limited by the length of the NMR tool antenna. As an example, the antenna of a MRIL Prime tool can be about 33 inches, while measured TOC values can be obtained from core plugs approximately 1 to 2 inches in length. During model training, the measured TOC values can be scaled to match the resolution of the NMR data.

Various techniques can be used to perform resolution-matching of the measured TOC values. In an example the measured TOC values can be resolution-matched by the arithmetic mean with a weighting function that is dependent of the distance between core samples if multiple core TOC data are available in the NMR vertical resolution window. If the core TOC values are more sparsely acquired than NMR vertical resolution, an interpolation may be applied to the core TOC data first. The variance in the resolution-matched core porosities can be similar to that in the NMR porosities.

In at least some embodiments, an RBF model developed using training data from one well can be used to predict TOC values from NMR data corresponding to another well. The accuracy of TOC prediction depends on the data of the training database and whether the two wells have similar characteristics. The RBF model developed using the training data from one well can be validated by predicting TOC values for another well. In such case, both wells have their own measured TOC values and NMR data. Alternatively the accuracy of an RBF model can be tested using the "leave one out" method and/or by dividing the data of the training database into two sets: one set for use in RBF model development, and another set for validation.

Figure 10:
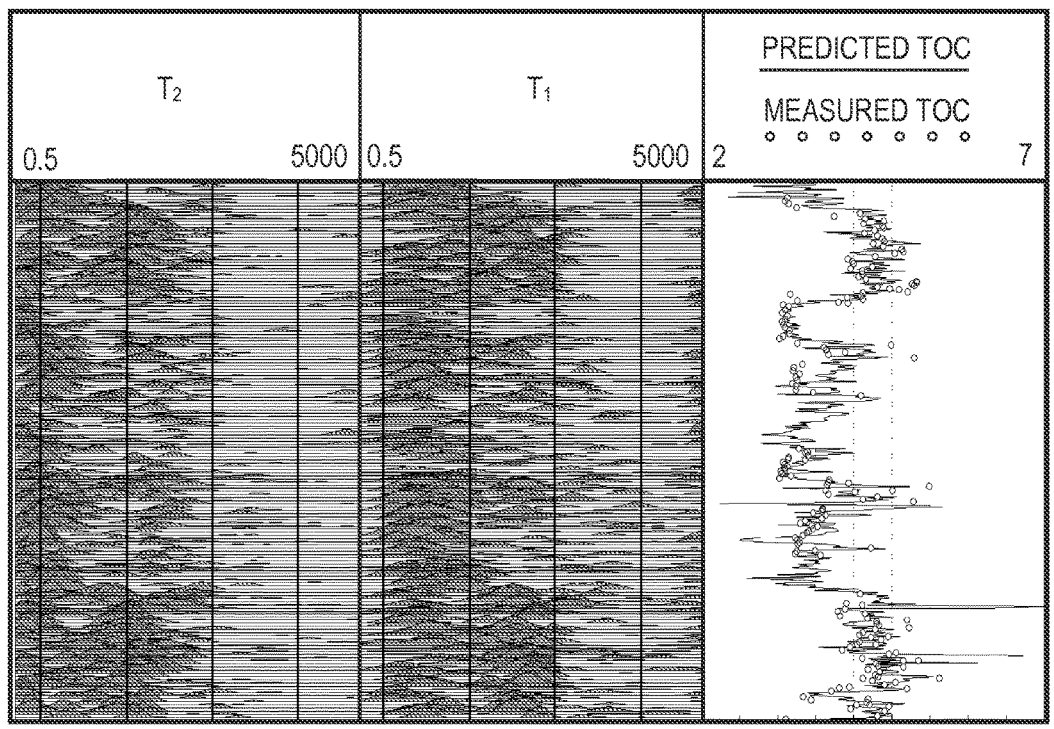
FIG. 10 is a plot showing an illustrative log of predicted TOC values and other data.

FIG. 10 is a plot 600 of an illustrative log of predicted TOC values as well as other data. In plot 600, $T_1$ and $T_2$ distributions as a function of measured depth are represented on the left side. Meanwhile, on the right side, the plot 600 displays predicted TOC values as a function of measured depth (the solid black line), and measured TOC values from a laboratory (the circles). Plots such as plot 600 may be displayed to an operator via a computer monitor, a tablet, or other processing device with a user interface. Based on such plots and/or other information, the operator may select to adjust RBF modeling and TOC prediction options, resulting in a plot with a modified predicted TOC values. Examples of adjustable settings include PCA parameters, RBF modeling parameters, data normalization, training data selection criteria, curve fitting parameters, etc. Further, such plots may be reported to a customer or otherwise used to generate a report for a customer.

Figure 11:
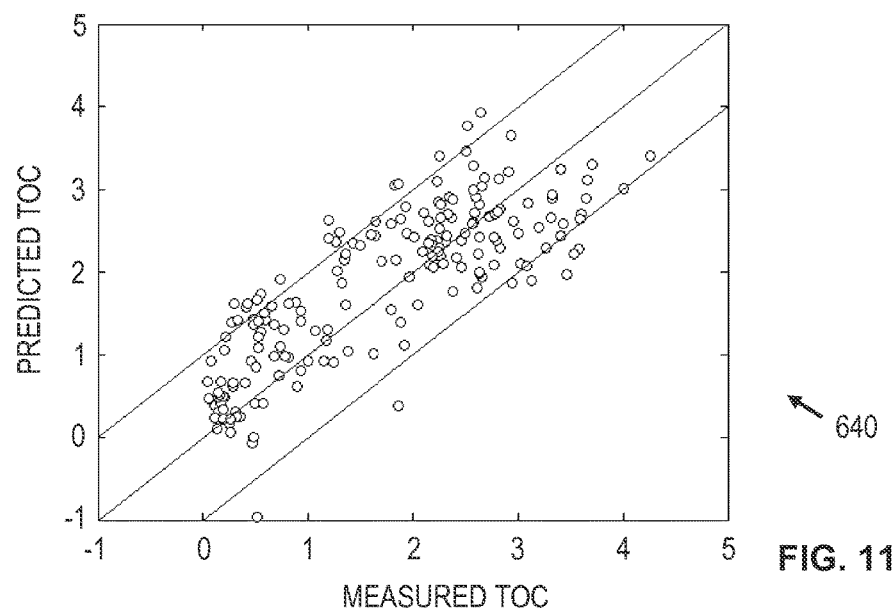
FIG. 11 is a graph showing predicted TOC values compared to measured TOC values.

FIG. 11 is a plot 640 showing a comparison of predicted TOC values and measured TOC values. Plots such as plot 640 may be generated to assess whether predicted TOC values have an acceptable degree of accuracy relative to measured TOC values. If so, the predicted TOC values are relied upon to generate reports, direct downhole tools, and perform field planning. On the other hand, if predicted TOC values do not have an acceptable degree of accuracy relative to measured TOC values, adjustments may be made to NMR data, NMR tool options, RBF modeling options, RBF model training options, etc.

Figure 12:
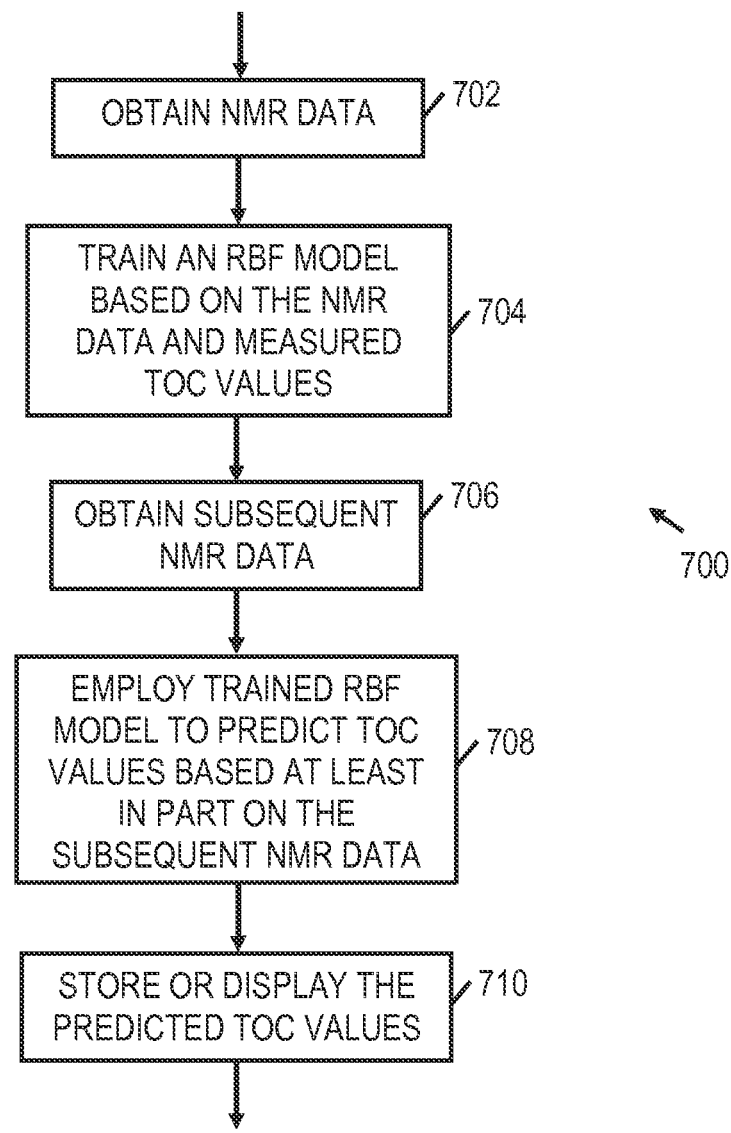
FIG. 12 is a flowchart showing an illustrative TOC prediction method.

FIG. 12 shows an illustrative TOC prediction method 700. At block 702, NMR data is obtained. As described herein, NMR data may correspond to raw NMR measurements and/or one or more types of processed NMR data obtained from downhole NMR logging tools or laboratory NMR tools. In at least some embodiments, the NMR data corresponds to relaxation-time distributions and/or PCA coefficients of relaxation-time distributions. At block 704, an RBF model is trained based on the NMR data and measured TOC values (e.g., obtained from a laboratory). The training step of block 704 may also involve use of gamma ray data, CBW values, porosity values, and/or other values. In some embodiments, the training data is derived solely from the NMR data. Alternatively, at least some of the training data may be derived independent of the NMR data. Various other options are possible for training an RBF model as described herein. Once RBF model training is complete, the types of data used for training are subsequently used for prediction (except that measured TOC values are no longer needed).

At block 706, subsequent NMR data is obtained. The subsequent NMR data and the NMR data using for training the RBF model may be obtained from the same NMR tool or different NMR tools. At block 708, the trained RBF model is employed to predict TOC values based at least in part on the subsequent NMR data. At block 710, the predicted TOC values are stored or displayed. For example, the predicted TOC values may be displayed as a log. Further, other data may be displayed along with the predicted TOC values to facilitate interpretation and analysis (see e.g., plots 600 and 640). As needed, adjustments are made to the RBF model, the type of training data used, and/or the input data for a trained RBF model. Such adjustments may be determined at least in part from displaying plots (see e.g., plots 600 and 640) or related data.

In accordance with at least some embodiments, the disclosed methods and systems related to predicting TOC values may be implemented in digital electronic circuitry, or in computer software, firmware, or hardware, including the structures disclosed in this specification and their structural equivalents, or in combinations of one or more of them. Computer software may include, for example, one or more modules of instructions, encoded on computer-readable storage medium for execution by, or to control the operation of, a data processing apparatus. Examples of a computer-readable storage medium include random access memory (RAM) devices, read only memory (ROM) devices, optical devices (e.g., CDs or DVDs), disk drives, etc.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read-only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 13:
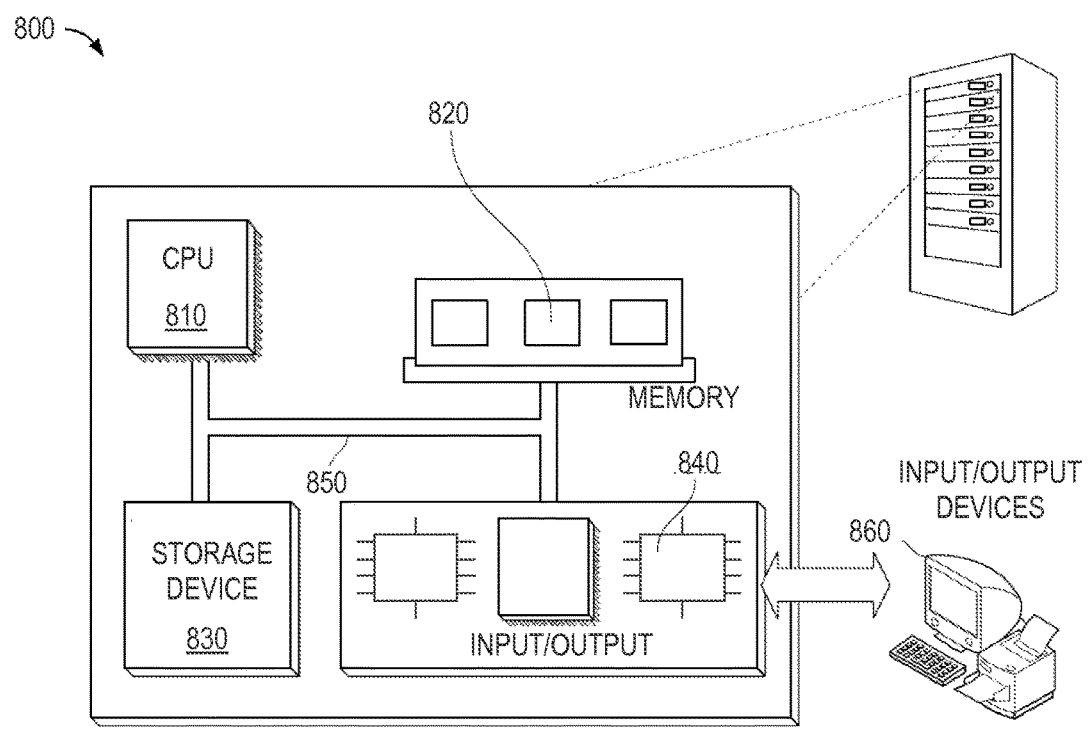
FIG. 13 is a diagram showing an illustrative computer system.

FIG. 13 shows an illustrative computer system 800. The computer system 800 may correspond to the computer system 42 mentioned in FIG. 1 and/or another computer system involved with collecting NMR measurements, processing NMR measurements, selecting training data from a database, constructing an RBF model, and/or using the RBF model to predict TOC values as described herein. The system 800 includes a processor 810, a memory 820, a storage device 830, and an input/output device 840. Each of the components 810, 820, 830, and 840 can be interconnected, for example, using a system bus 850. The processor 810 is capable of processing instructions for execution within the system 800. In some embodiments, the processor 810 is a single-threaded processor, a multi-threaded processor, or another type of processor. The processor 810 is capable of processing instructions stored in the memory 820 or on the storage device 830. The memory 820 and the storage device 830 can store information within the computer system 800.

The input/output device 840 provides input/output operations for the system 800. In some embodiments, the input/output device 840 can include one or more network interface devices, e.g., an Ethernet card; a serial communication device, e.g., an RS-232 port; and/or a wireless interface device, e.g., an 802.11 card, a 3G wireless modem, a 4G wireless modem, etc. In some embodiments, the input/ output device can include driver devices configured to receive input data and send output data to other input/output devices, e.g., keyboard, printer and display devices 860. In some embodiments, mobile computing devices, mobile communication devices, and other devices can be used.

The disclosed options for predicting TOC values should not be construed as limitations on the scope of what may be claimed, but rather as descriptions of features specific to particular examples. Certain features that are described in this specification in the context of separate embodiments can also be combined. Conversely, various features that are described in the context of a single embodiment can also be implemented in multiple embodiments separately or in any suitable combination.

Embodiments disclosed herein include:

A: A method that comprises obtaining NMR data and training an RBF model based on the NMR data and measured TOC values. The method also comprises obtaining subsequent NMR data and employing the trained RBF model to predict TOC values based at least in part on the subsequent NMR data. The method also comprises storing or displaying the predicted TOC values.

B: A system that comprises at least one processor and a memory in communication with the at least one processor and storing instructions. When executed, the instructions cause the at least one processor to obtain NMR data, to train an RBF model based on the NMR data and measured TOC, to obtain subsequent NMR data, to employ the trained RBF model to predict TOC values based at least in part on the subsequent NMR data, and to store or display the predicted TOC values.

Each of the embodiments, A and B, may have one or more of the following additional elements in any combination. Element 1: further comprising displaying a TOC log that plots the predicted TOC values as a function of measured depth. Element 2: further comprising displaying a chart that compares the predicted TOC values with measured TOC values. Element 3: further comprising adjusting the trained RBF model or inputs to the trained RBF model based on a comparison of the predicted TOC values with measured TOC values. Element 4: further comprising obtaining porosity values independent of the NMR data, and training the RBF model to predict TOC values based on the porosity values. Element 5: further comprising obtaining CBW values, training the RBF model to predict TOC values based on the CBW values, obtaining subsequent CBW values, and employing the trained RBF model to predict TOC values based at least in part on the subsequent CBW values. Element 6: further comprising obtaining gamma ray logging data, training the RBF model based on the gamma ray logging data, obtaining subsequent gamma ray logging data, employing the trained RBF model to predict TOC values based at least in part on the subsequent gamma ray logging data. Element 7: further comprising training the RBF model to predict TOC values based on principal components representing an NMR relaxation-time distribution. Element 8: wherein obtaining the NMR data comprises collecting NMR measurements by a downhole logging tool, deriving an NMR relaxation-time distribution based on the collected NMR measurements, and determining principal components of the NMR relaxation-time distribution. Element 9: wherein obtaining the NMR data comprises determining an arithmetic or geometric means of an NMR relaxation-time distribution. Element 10: wherein obtaining the NMR data comprises determining or receiving a ratio of different NMR relaxation-time distributions.

Element 11: wherein the instructions, when executed, further cause the at least one processor to obtain gamma ray logging data, to train the RBF model based on the gamma ray logging data, to obtain subsequent gamma ray logging data, and to employ the trained RBF model to predict TOC values based at least in part on the subsequent gamma ray logging data. Element 12: wherein the instructions, when executed, further cause the at least one processor to obtain CBW values, to train the RBF model to predict TOC values based on the CBW values, to obtain subsequent CBW values, and to employ the trained RBF model to predict TOC values based at least in part on the subsequent CBW values. Element 13: wherein the instructions, when executed, further cause the at least one processor to train the RBF model to predict TOC values based on a principal components representing an NMR relaxation-time distribution. Element 14: wherein the instructions, when executed, further cause the at least one processor to provide a user interface that enables an operator to adjust training data used to train the RBF model. Element 15: wherein the instructions, when executed, further cause the at least one processor to provide a user interface that enables an operator to adjust the RBF model. Element 16: wherein the instructions, when executed, further cause the at least one processor to provide a user interface that enables an operator to adjust principal component analysis (PCA) operations applied to training data for the RBF model or input data for a trained RBF model. Element 17: further comprising a display in communication with the at least one processor to display a TOC log that plots the predicted TOC values as a function of measured depth. Element 18: further comprising a downhole NMR logging tool in communication with the at least one processor to collect NMR measurements from which the obtained NMR data is derived.

Numerous variations and modifications will become apparent to those skilled in the art once the above disclosure is fully appreciated. It is intended that the following claims be interpreted to embrace all such variations and modifications.

What is claimed is:

1. A method that comprises:
    obtaining nuclear magnetic resonance (NMR) data through a downhole logging tool;
    training a radial basis function (RBF) model based on the NMR data and measured total organic carbon (TOC) values, wherein training the RBF model comprises:
    obtaining subsequent NMR data; and
    applying a principal component analysis process on the NMR data and retaining a small number of principal components;
    employing the trained RBF model to predict TOC values based at least in part on the subsequent NMR data; and
    storing or displaying the predicted TOC values, wherein the predicted TOC values correspond to a rock sample or subsurface formation volume.

2. The method of claim 1, further comprising displaying a TOC log that plots the predicted TOC values as a function of measured depth.

3. The method of claim 1, further comprising displaying a chart that compares the predicted TOC values with measured TOC values.

4. The method of claim 1, further comprising adjusting the trained RBF model or inputs to the trained RBF model based on a comparison of the predicted TOC values with measured TOC values.

5. The method of claim 1, further comprising obtaining porosity values independent of the NMR data, and training the RBF model to predict TOC values based on the porosity values.

6. The method of claim 1, further comprising:
obtaining clay bound water (CBW) values;
training the RBF model to predict TOC values based on the CBW values;
obtaining subsequent CBW values; and
employing the trained RBF model to predict TOC values based at least in part on the subsequent CBW values.

7. The method of claim 1, further comprising:
obtaining gamma ray logging data;
training the RBF model based on the gamma ray logging data;
obtaining subsequent gamma ray logging data; and
employing the trained RBF model to predict TOC values based at least in part on the subsequent gamma ray logging data.

8. The method of claims 1, further comprising training the RBF model to predict TOC values based on principal components representing an NMR relaxation-time distribution.

9. The method of claim 1, wherein obtaining the NMR data comprises:
collecting NMR measurements by a downhole logging tool;
deriving an NMR relaxation-time distribution based on the collected NMR measurements; and
determining principal components of the NMR relaxation-time distribution.

10. The method of claim 1, wherein obtaining the NMR data comprises determining an arithmetic or geometric means of an NMR relaxation-time distribution.

11. The method of claim 1, wherein obtaining the NMR data comprises determining or receiving a ratio of different NMR relaxation-time distributions.

12. A system that comprises:
at least one processor;
a memory in communication with the at least one processor and storing instructions that, when executed, cause the at least one processor to:
obtain nuclear magnetic resonance (NMR) data;
train a radial basis function (RBF) model based on the NMR data and measured total organic carbon (TOC) values, wherein training the RBF model comprises:
obtaining subsequent NMR data; and
applying a principal component analysis process on the subsequent NMR data and retaining a small number of principal components;
employ the trained RBF model to predict TOC values based at least in part on the subsequent NMR data; and
store or display the predicted TOC values, wherein the predicted TOC values correspond to a rock sample or subsurface formation volume.

13. The system of claim 12, wherein the instructions, when executed, further cause the at least one processor to:
obtain gamma ray logging data;
train the RBF model based on the gamma ray logging data;
obtain subsequent gamma ray logging data; and
employ the trained RBF model to predict TOC values based at least in part on the subsequent gamma ray logging data.

14. The system of claim 12, wherein the instructions, when executed, further cause the at least one processor to:
obtain clay bound water (CBW) values;
train the RBF model to predict TOC values based on the CBW values;
obtain subsequent CBW values; and
employ the trained RBF model to predict TOC values based at least in part on the subsequent CBW values.

15. The system of claim 12, wherein the instructions, when executed, further cause the at least one processor to train the RBF model to predict TOC values based on principal components representing an NMR relaxation-time distribution.

16. The system of claim 12, wherein the instructions, when executed, further cause the at least one processor to provide a user interface that enables an operator to adjust training data used to train the RBF model.

17. The system of claim 12, wherein the instructions, when executed, further cause the at least one processor to provide a user interface that enables an operator to adjust the RBF model.

18. The system of claim 12, wherein the instructions, when executed, further cause the at least one processor to provide a user interface that enables an operator to adjust principal component analysis (PCA) operations applied to training data for the RBF model or input data for a trained RBF model.

19. The system of claim 12, further comprising a display in communication with the at least one processor to display a TOC log that plots the predicted TOC values as a function of measured depth.

20. The system of claim 12, further comprising a downhole NMR logging tool in communication with the at least one processor to collect NMR measurements from which the obtained NMR data is derived.

* * * * *